United States Patent
Cavallaro

[11] Patent Number: 5,718,012
[45] Date of Patent: Feb. 17, 1998

[54] METHOD OF STRENGTH ENHANCEMENT OF COLLAGEN CONSTRUCTS

[75] Inventor: John F. Cavallaro, Lexington, Mass.

[73] Assignee: Organogenesis, Inc., Canton, Mass.

[21] Appl. No.: 652,666

[22] Filed: May 28, 1996

[51] Int. Cl.⁶ .................. A61L 17/00; A63B 51/02; D01C 3/00

[52] U.S. Cl. .................. 8/94.11; 8/94.1; 8/127.5; 623/11

[58] Field of Search ............. 623/11, 13; 128/DIG. 8; 8/94.1, 94.11, 127.5, 127.51, 127.6, 130.1

[56] References Cited

U.S. PATENT DOCUMENTS

| | | | |
|---|---|---|---|
| 3,166,074 | 1/1965 | Kurilla | 8/127.5 |
| 3,483,286 | 12/1969 | Duffy et al. | 8/94.11 |
| 3,625,811 | 12/1971 | Okamura | 8/127.5 |
| 4,209,859 | 7/1980 | Hoffman | 623/13 |
| 5,106,949 | 4/1992 | Kemp et al. | 530/356 |
| 5,171,273 | 12/1992 | Silver et al. | 623/13 |
| 5,263,984 | 11/1993 | Li et al. | 623/13 |
| 5,281,422 | 1/1994 | Badylak et al. | 623/11 |
| 5,308,889 | 5/1994 | Rhee et al. | 604/11 |
| 5,378,469 | 1/1995 | Kemp et al. | 623/16 |

*Primary Examiner*—Paul B. Prebilic
*Attorney, Agent, or Firm*—Hale and Dorr LLP

[57] ABSTRACT

A method for improving the tensile strength of wet collagen threads or collagen thread constructs for implantation to replace or repair tissue or organs wherein the strength of the threads is improved by plasticizing the threads with a plasticizing agent, imparting a tensile load to the collagen thread to strain the collagen thread; allowing the load in the thread to decrease by stress-relaxation or by creep conditioning methods and finally, removing the plasticizing agent. Prosthetic devices comprising collagen threads with improved strength characteristics are intended to repair load bearing tissues such as ligaments and tendons.

22 Claims, No Drawings

METHOD OF STRENGTH ENHANCEMENT OF COLLAGEN CONSTRUCTS

FIELD OF THE INVENTION

The present invention is in the field of tissue engineered implantable medical devices and is directed to prosthetic devices made from collagen threads which are used to replace or repair tissue or organs. Such prosthetic devices are intended to repair load bearing tissues such as ligament and tendon, for example. This invention describes a method for improving the ultimate tensile stress (UTS) of collagen threads and collagen thread constructs by using stress relaxation.

BACKGROUND OF THE INVENTION

One of the most important attributes of living organisms is their capacity for self-repair. Several mechanisms have evolved to achieve this, including wound healing, compensatory growth and epimorphic regeneration. (J. Gross, Regeneration versus repair, pp. 20–39 (1992), In: L. K. Cohen, R. F. Diegelman and W. J. Lindblad (eds.), Wound Healing: Biochemical and Clinical aspects, W. B. Saunders, Philadelphia). Although all tissues and organs (with the possible exception of teeth) are capable of some degree of repair, mammals have unfortunately lost the ability to faithfully regenerate severely damaged body parts. (J. Gross, supra (1992)). In an attempt to overcome this deficiency, numerous synthetic devices have been developed, with the intention that the implants be biologically inert, and yet function for the lifetime of the recipient. Experience with synthetic devices, however, has shown that not only is biological inertness apparently impossible, but the interaction between a biomaterial and the surrounding living tissue can actually contribute to the long-term success of the implant. (J. Kohn, Med. Dev. Technol., 1:34–38 (1990)). The science of tissue engineering has arisen to exploit this biological reality.

The biomaterials used to produce bioremodelable grafts are the focus in this area of study. Two families of materials are being evaluated by a number of investigators: biological components of the extracellular matrix (ECM), such as collagen and proteoglycan, and synthetic, non-biological materials. Biological derived materials are advantageous in that they contain properties that facilitate cell attachment and function, whereas synthetics may not interact with cells in the desired manner (R. Langer, Science, 260:920–926 (1993)). Investigators are also attempting to alter synthetics by coupling peptide sequences recognized by cell adhesion proteins such as the integrins (J. A. Hubbell, Ann NY Acad Sci, 665:253–258 (1992); Lin, H. B., et al., Biomaterials, 13:905–914 (1992)).

The original theory that the extracellular matrix is merely an inert supporting material in or on which cells reside has recently been regarded as false (Hay, E. D., et al., Cell Biology of the Extracellular Matrix, 2nd edition (1991), Plenum Press, New York; Nathan, C., J Cell Biol, 113:981–986 (1991)). Cells continue to interact with the many components of the extracellular matrix, which continue to serve the functions of adhesive, biomaterial, filter, receptor, signal and text (Nathan, C., supra (1991); Trelstad, R. L., Textbook of Rheumatology, pp. 35–57 (1993) 4th edition, W. B. Saunders, Philadelphia). Therefore, it seems reasonable to suppose that the complex interaction between the cells and the extracellular matrix are such that the biologically derived implants will continue to provide stimuli to guide remodeling, that synthetics cannot, unless they are modified to such an extent that they become essentially identical to the natural molecules they are attempting to mimic.

Although biologic in origin, extensive chemical modification of collagen tends to render it as "foreign". To improve the long term performance of implanted collagenous devices, it is important to retain many of the properties of the natural collagenous tissue. In this "tissue engineering" approach, the prosthesis is designed not as a permanent implant but as a scaffold or template for regeneration or remodeling. Tissue engineering design principles incorporate a requirement for isomorphous tissue replacement, wherein the biodegradation of the implant matrix occurs at about the same functional rate of tissue replacement by the host so that a functional analog of the original tissue results. (Yannas, I. V. (1995) Regeneration Templates. pp. 1619–1635. In: Bronzino, J. D. (ed.), The Biomedical Engineering Handbook, CRC Press, Inc., Boca Raton, Fla.)

Although Type I collagen has been utilized as a biomaterial for over 50 years, such implants have not generally exploited the body's ability to remodel an implant. On the contrary, implants were intended to be permanent, and the manufacturing process used to produce these devices either utilized partially degraded, enzyme-extracted collagen, stabilized the collagen by crosslinking it using glutaraldehyde or chromium salts (Chvapil, M., Industrial uses for collagen., In D. A. D. Parry and L. K Creamer (eds.), Fibrous proteins: scientific, industrial and medical aspects, (1979) Academic Press, London.; Chvapil, M., Int Rev Connect Tiss Res, 6:1 (1972); Stenzel, K. H., et al., Ann Rev Biophys Bioeng, 3:231–253 (1974)), or assembled the collagen into non-natural polymeric structures such as films and sponges (Burke, J. F., supra (1981); Chvapil, M., supra (1979); Chvapil, M. (1973), supra, Rubin, A., J Macromol Sci Chem., A3:113–118 (1969); Stenzel, K. H., supra (1974); Yannas, I. V., Science, 215:174–176 (1982); Yannas, I. V., Proc Natl Acad Sci USA, 86:933–937 (1989); Heimbach, D., Ann Surg, 208:313–320 (1988)). Since prosthetics that must function under significant loads require significant mechanical strength, such as ligaments and tendon replacements and in hernia repair, alternative biomaterials are being sought.

An important area for tissue engineering is the development of a material to permanently replace a damaged ligament or tendon. The tendon or ligament replaced most commonly is the anterior cruciate ligament (ACL) of the knee, due to damage commonly attributed to athletic injuries such as football or skiing. Once the ACL is torn, healing does not occur by itself as it may in other knee ligaments (e.g., the medial collateral ligament) primarily because apposition of the torn ligament stumps is impossible due to elastic contraction.

Patellar tendon autografts are the current standard of care for anterior cruciate ligament (ACL) replacement (Markolf KL et al. Trans ORS 20: 644, 1995). Autografts are not regulated medical devices and are not subject to any manufacturing and marketing regulations that govern biomaterials. Patellar tendon is readily available for use by the surgeon and being autograft material, immunological rejection is not a concern. Typically, a slice of patellar tendon one-third of its width is removed from the same knee joint and is placed in the anterior cruciate position; fixation is usually accomplished by precise drilling into the femur and tibia, placing the graft between, and fixing the ends in bone cement within the drilled holes. Although functional as a scaffold for tissue regrowth and biological fixation, the harvesting procedure causes additional trauma to the ACL patient. Moreover, the patellar tendon is weakened during the remodeling process and may then be damaged. Ultimately, the failure rate of patellar tendon autografts is high because they are slow to revascularize, and often elongate to the point where knee loads are no longer supported.

After the failure of a patellar tendon autograft, surgeons consider a prosthetic device for ACL replacement. Advances in materials science have produced grafts which are very strong and durable, even surpassing the natural strength of the ACL. The primary materials considered for ACL replacement grafts are synthetic polymers, carbon fibers, and collagen.

Allogeneic materials (i.e., cadaveric grafts) avoid harvest trauma, but may carry risks of transmission of viral pathogens. Synthetic graft material, generally polyethylene teraphthalate (Dacron, manufactured by both Howmedica and Stryker) or polytetrafluoroethylene (Teflon, made by Gore-Tex), and carbon fiber grafts (DuPont) can be twice as strong as native ACL tissue and can endure up to $1 \times 10^7$ cycles without failure. However, bench tests cannot simulate the internal milieu of the knee joint. Although these grafts start out strong enough to bear the required loading, these materials are not biologically inert and are subject to fatigue and abrasion. Problems of chronic inflammation and abrasion persist and worsen with time until mechanical failure occurs, necessitating re-operation.

ACL grafts made from reconstituted collagen fibers have been reported. U.S. Pat. No. 5,171,273 disclosed a collagen graft comprising synthetic collagen fibers embedded in a loose uncrosslinked collagen matrix. The starting material for the fibers was insoluble collagen dissociated from bovine corium (dermis). The dissociated material is a suspension of fragments of native banded, fibrillar bovine type I collagen which is believed to contain small amounts of other tissue proteins.

U.S. Pat. No. 5,263,984 disclosed a prosthetic ligament comprising filaments formed of fibrils or short pieces of native polymeric connective tissues such as collagen. The starting collagen material in the case was also insoluble.

Reconstituted collagen fibers arranged in bundles (Dunn, F. H., et al. Am J Sports Med 20: 507, 1992. Cavallaro, J. F. et al. Biotech Bioeng 43: 781, 1994.) or braids (Cavallaro, J. F., et al. supra. Chvapil, M., et al. J Biomed Mat Res 27: 313, 1993.) have been proposed as ACL replacements with tissue engineering properties. Promising implant studies in smaller animal models such as the rabbit (Dunn, F. H., et al. supra) and dog (Cavallaro, J. F., et al. supra) have not yet succeeded in larger models as in the goat (Chvapil, M., et al. supra), perhaps because of the relatively low cooperative strength of the composite structure, despite the high ultimate tensile stress (UTS) of the individual fibers. This loss of strength is due to uneven tensions, lengths, and orientations among the fibers in the construct (Zurek W., et al. Textile Res J 57(8): 439, 1987.)

It is desirable to have a prosthetic device prepared from a biomaterial such as collagen that approaches the strength of synthetic materials. It is a continuing goal of researchers to develop implantable prostheses which can successfully be used to replace or repair mammalian tissues.

SUMMARY OF THE INVENTION

The invention provides a method for improving the tensile strength of collagen threads and constructs that are made from collagen threads that includes plasticizing a collagen thread or thread construct with a plasticizing agent; imparting a tensile load to the collagen thread or construct to strain the collagen thread and then allowing the strain in the thread to decrease by stress-relaxation or by creep. Additionally the method can include crosslinking the thread at the length with a crosslinking agent.

Collagen threads and constructs comprising collagen threads with improved tensile strength properties are useful for implantation as a prosthetic device. Prosthetic devices comprising collagen threads with improved strength characteristics are intended to repair load bearing tissues such as ligament and tendon.

DETAILED DESCRIPTION OF THE INVENTION

The present invention provides methods for increasing the strength of biocompatible prosthetic devices comprising collagen threads useful as implants for repairing damaged tendons, ligaments and other structures for hernia repair, blood vessel replacement, prolapse support and chest wall reconstruction after trauma or tumor resection. In one preferred embodiment, the ligament replaced is the anterior cruciate ligament (ACL) in the knee joint of mammals.

The devices of the present invention comprise and arrangement of collagen threads formed from a solution of collagen molecules that mimic the chemical and organizational structure of natural collagen. In one preferred embodiment, the device comprises collagen threads, arranged in a bundle in which the collagen threads have been conditioned stress-relaxation to improve the tensile strength of the device. Once implanted, the device provides a scaffold for the infiltration and population for host connective tissue cells that eventually supplement or replace the device with natural tissue, thus allowing it to perform its natural functions.

Collagen threads comprising collagen may be prepared by any number of methods known in the art of collagen thread formation. In accordance with the present invention, acid extraction rather than enzyme extraction is preferably used to produce the collagen solution. Enzyme extraction (pepsin) removes the telopeptide regions from the ends of the collagen molecule; such collagen preparations produce weaker threads than do acid extracted preparations. Similarly, pepsin extracted collagen has been shown to produce fibroblast contracted collagen lattices which are twenty times weaker than lattices produced from acid extracted collagen (Bell, E., INSERM, 177:13–28 (1989)). Acid solubilized collagen can be prepared using techniques and sources known to the skilled artisan. Sources of collagen include skin and tendon. A preferred collagen composition for use herein is obtained from a novel source, the bovine common digital extensor tendon, and by a novel extraction method, both as disclosed in U.S. Pat. No. 5,106,949, the disclosure of which is incorporated herein by reference. Although monomers and mixtures of monomers and higher ordered collagen polymers, e.g., dimers up to and including fibrils, can be used in the practice of the present invention; monomers are preferred for many applications.

Collagen solutions for use in the present invention are generally at a concentration of about 2 to 10 mg/mL, preferably from about 4 to 6 mg/mL, and most preferably at about 4.5 to 5.5 mg/mL and at a pH of about 2 to 4. A preferred solvent for the collagen is dilute acetic acid at about 0.05 to about 0.1% v/v. Other conventional solvents for collagen may be used as long as the solvents are compatible with thread formation and the desired properties of the collagen thread. These collagen solutions may also contain optional components known to those of ordinary skill in the art to modify or regulate the interaction between the host and the implant; components such as neutral and charged polymers, including but not limited to polyvinyl alcohol, polyethylene glycol, hyaluronic acid, growth factors, and other extracellular matrix components such as proteoglycans.

The formation of collagen threads using acid solubilized type I collagen is described in U.S. Pat. No. 5,378,469, incorporated herein by reference. One preferred method of making collagen threads for use in the present invention comprises:

(a) extruding a solution comprising collagen into a dehydrating agent, the dehydrating agent having a higher osmotic pressure than that of the collagen solution and a pH of about 5 to 9; and, (b) maintaining the dehydrating agent under conditions to enable collagen thread formation.

In another preferred method of making collagen threads, the method further comprises rinsing formed thread of the dehydration agent to provide additional flexibility. This optional step is particularly useful in application wherein the collagen thread is to be knitted or woven. One preferred rinse agent is purified water. Another preferred rinse agent comprises phosphate buffered saline (PBS) having a phosphate concentration of about 0.001 to about 0.02M and a sodium chloride (NaCl) concentration of about 0.05 to about 0.1M. When buffered solutions are used, the pH of the rinsing bath is kept above a pH of about 5 to prevent over-hydration of the thread. A preferred pH range is from about 6 to about 8.

Properties of collagen threads and fibers can be evaluated similarly to other threads and fibers used in the textile industry. Textile fibers are generally measured as thread mass per length, or denier (mass in grams per 9000 meters of length). Typically between about 40 to 80, the denier can be varied from about 15 to about 300 by altering the collagen infusion rate to the dehydration bath, the flow rate of the dehydration bath, and/or the needle (orifice) size. The tenacity of a thread is measured as grams of pull strength per denier. For example, if a 50 denier thread has a pull strength of 220 grams, the tenacity is 220/50=4.40 grams per denier (gpd). Ultimate load is the maximum load of a thread or thread construct, just before breaking, usually measured in grams. Ultimate Tensile Stress (UTS) is calculated by dividing the ultimate load by the cross sectional area and is measured in Newtons per square millimeter which is also termed as mega Pascals (MPa), or in pounds per square inch (psi). Grams per denier (gpd) can also be used to express UTS.

Constructs may be formed from collagen threads by techniques for processing fibers known to those skilled in the art, e.g., knitting and weaving. Most fiber handling techniques for both natural fibers, e.g., cotton, silk, etc., and synthetic fibers, e.g., nylon, cellulose acetate, etc., should be useful in processing threads provided herein, including techniques used to produce three-dimensional textiles. See, e.g., Mohamed, American Scientist, 78, (1990) 530–541. Three-dimensional collagen constructs and methods for making them are disclosed in U.S. Ser. No. 08/215,760, the disclosure of which is incorporated herein.

Collagen threads have been used to form braided constructs, plied into yarn, and knitted as disclosed in U.S. Ser. No. 08/216,527. The collagen threads can be woven using techniques known to the skilled artisan to produce a woven construct. A knitted tube comprising two-ply yarn, a twist of one crosslinked collagen thread and one non-crosslinked collagen thread has been used in the preparation of a blood vessel construct also described in U.S. Ser. No. 08/216,527.

In a preferred embodiment, a multi-filament bundle is formed by winding the threads around a fixture comprising at least two points, such as pegs firmly mounted to a frame, to produce a closed loop. When the closed loop is removed from the pegs, the opposing sides of the loop are brought together so that the bulk of the threads are in parallel to each other to form two loops at either end of the bundle. The loops at either end of the bundle are then secured and either or both loops may then optionally be cut to form a bundle of individual collagen thread segments that are nearly about the same length. A loop or loops at either end of the construct may be used to fixture the bundled construct when implanted or engrafted into a host or patient. To form a 500-ply bundle by this method, the thread is wound around the fixture 250 times. Bundles may also be formed by gathering and aligning the ends of individual thread segments that are comparably about the same length and then securing the ends to form a bundled construct. Other techniques and sources known to the skilled artisan may also be used to form a thread bundle. A bundle can be used to form a multi-filamented braid of three or more bundles of threads, a two or more bundle helix, or a single twisted bundle or untwisted bundle. At least one loop may also be formed at an end of the bundle to provide a means for fastening the device when implanted into a host or patient.

The theoretical strength of identical collagen fibers bundled in parallel surpasses that of any twisted or braided construct containing the same number of fibers, due to the fact that any twisted or braided construct contains elements not truly aligned with the axis of the construct. In practice, however, braids and twisted constructs often have the ability to bear much higher tensile loads than parallel bundles, because it is impossible to maintain absolutely uniform fiber lengths and tensions across the bundle.

One approach to combat the practical loss of strength in a parallel bundle of collagen threads is to leverage two important properties of collagen: it is readily plasticized, and imposed stress readily relaxes with time. The viscoelasticity of collagenous tissues was investigated by Fung who defines stress relaxation, also simply termed as "relaxation", as a process when a tissue is loaded at a constant finite strain and length is held constant, the corresponding stresses induced in the tissue decrease with time. (Fung, Y. C., (1981) Biomechanics: Mechanical Properties of Living Tissues. pp. 211 Springer-Verlag New York Inc., New York) Thus, by first plasticizing and then elongating or extending a parallel bundle of non-crosslinked collagen fibers, all of the fibers are brought to the same length. Then, if the stressed bundle is allowed to relax, the effect is all the fibers are brought to about the same degree of tension. Alternatively, after plasticizing, the construct can be allowed to creep (i.e., elongate under tensile load) thus achieving the same result. At the ultrastructural level, these conditioning treatments of stress-relaxation and creep cause the collagen molecules within the fiber to align with the fiber axis; indeed, for the same reason, fiber drawing is a well known method to improve tensile properties (Zurek, supra) These conditioning treatments have the added benefit of aligning the bundle elements together into a more coherent unit by increasing the packing density of the fibers. Coherence of the construct permits load sharing between adjacent collagen threads to contribute to the strength of the construct. With coherence, the packing density (also termed "fiber volume") is increased, and more threads can be made to fit in a confined space such as a joint or bone tunnel when implanted as a ligament prosthesis. These factors combine to significantly improve the wet strength of a bundled collagen fiber construct.

In the preferred embodiment, a single collagen thread or collagen thread bundle of between 2 and 1000-ply is produced by bundling methods known in the art. Each thread in the bundle is preferably about the same length as compared to others in the bundle. The threads may, however be of varying denier and composition. For example, the orientation of the threads in the bundle may be so that the core of the bundle is composed of thinner or lower denier threads and the peripheral threads are thicker or higher denier threads. The composition of either the inner or outer threads in a bundle may have cytokines or growth factors coated on or incorporated within the threads to improve or regulate cell compatibility or bioremodeling. The bundle may also be modified so that the ends of the bundle that are implanted within bone are treated with a bone morphogenic protein or cytokines that enhance bone formation.

The bundle is then placed within a device that can pull the bundle form the ends in opposite directions to impose a strain along the length of the bundle. The baseline value of tensile strength for dry, non-crosslinked bundles is obtained by pulling the bundles past the breaking point, noting the peak load.

The method for improving the tensile strength of a collagen thread or bundle comprising collagen threads comprises fixing the ends of a thread bundle in a device or means for pulling the bundle by the ends in opposite directions. A preferred device for pulling the bundle by the ends is a mechanical testing system such as the Mini-Bionix 858 mechanical testing system (MTS Systems Corp., Eden Prairie, Minn.). Once the ends of the bundle are fixed by the grips of the mechanical testing system, the bundle is then plasticized. Plasticizing agents are preferably water or aqueous solutions or buffers such as phosphate buffered saline (PBS). Buffered solutions with lower pH have been used to plasticize the collagen threads at a faster rate than those of higher pH. Plasticizing agents such as glycerol or other hygroscopic agents known in the art may possibly be used, but in order for strength to be preserved after conditioning treatment, the plasticizer must also be removed.

Once plasticized, the bundles are elongated by the mechanical testing system to impart a total strain of preferably between about 20 to 200%, more preferably between about 50 to 100%. The elongation step can be done incrementally or in a stepwise manner by elongation to impart a strain of about 5 to 10% and allowed to relax to decrease the stress in the construct to between about 0.5 and zero grams per end before further elongation. Alternatively, (as in creep) a tensile load can be applied and maintained while the length is increased. The stress in the bundled thread construct is preferably allowed to relax or dissipate to about zero load. The less stress remaining after relaxation, the greater affect on increasing strength the conditioning will have.

The stress-relaxed or creep conditioned construct is preferably crosslinked after conditioning treatment. Crosslinking provides strength, stability and some durability to collagen threads and constructs that comprise collagen. Crosslinking is accomplished by any number of methods known to those of ordinary skill in the art, including lyophilization, ultraviolet (UV) irradiation, or contacting the construct chemical crosslinking agent. Various types of chemical crosslinking agents are known in the art and can be used such as acyl-azide, hexamethylene diisocyanate, bisimidates, glyoxal, polyglycerol polyglycidyl ether, adipyl chloride, ribose and other sugars, carbodiimides such as cyanamide or 1-ethyl-3-(3-dimethylaminopropyl) carbodiimide hydrochloride (EDC), aldehydes such as glutaraldehyde or formaldehyde, and oxidative agents may be used. Preferred crosslinking agents are those that produce a biocompatible material capable of being remodeled by host cells. A preferred crosslinking agent is EDC. Carbodiimides activate carboxyl groups on the collagen molecule which then form synthetic peptide bonds with adjacent amino groups, releasing a urea. The crosslinking solution containing EDC and water may also contain acetone. In a preferred embodiment, sulfo-N-hydroxysuccinimide is added to the crosslinking agent (Staros, 1982). However, crosslinking agents need not be limited to these examples as other crosslinking agents and methods known to those skilled in the art may be used.

The ultimate tensile strength (UTS) increase of stress-relaxation conditioned collagen thread bundles over non-stress-relaxation conditioned collagen thread bundles is due to the improved alignment and the reduction in total cross sectional area (i.e., fiber thinning) caused by the elongation treatment. The UTS increase of stress-relaxation conditioned collagen thread bundles over denier matched controls appears to be due to improved load sharing, as length, tension, and orientation become more uniform within the bundle.

The strength enhanced collagen threads of the invention are preferably sterilized prior to implant or engraftment to a patient or host. Sterilization may be achieved by use of gamma irradiation with typically 2.5Mrad, ethylene oxide, or by chemical sterilization. A preferred method of chemical sterilization of the stress relaxed collagen construct is by contact of the construct with dilute peracetic acid solution with a neutral pH or high salt concentration. Methods for sterilizing collagen are described in U.S. Pat. No. 5,460,962, the disclosure of which is incorporated by reference herein. However, sterilants and methods of sterilization are not so limited by these examples as other sterilants and methods for sterilizing collagen are known to those skilled in the art may alternatively be used.

The collagen fibers may also be coated with agents such as pharmaceuticals; growth factors; hormones; other extracellular matrix components; or genetic material. Coating of the agent can be achieved by immersion or chemical binding. Coatings can be selected as to affect the bioremodelability of the construct by promoting or regulating host cell ingrowth. Prior to implantation into a host or patient, cells may be cultured on the fibers as collagen is a natural substrate for cells to bind.

The following examples are provided to better explain the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

Fabrication of Reconstituted Collagen Threads

Collagen threads were prepared according to U.S. Pat. No. 5,378,469, the disclosure of which is incorporated herein. The fabrication of collagen threads is briefly described below.

A. Materials and Equipment:

1. Collagen: Acid extracted collagen, as prepared in U.S. Pat. No. 5,106,949, was stored at 4° C. in 0.05% acetic acid at a concentration of 5.0 mg/mL and was degassed prior to use.

2. 140 cc syringe (Becton Dickinson).

3. Blunt stainless steel needle, 18 gauge (Popper & Sons, Inc.), with silicone leader tubing and bridge.

4. Syringe Pump.

5. An 18 foot long PVC dehydration trough 2 inches in diameter, with Masterflex Pump and norprene tubing.

6. Dehydration agent: prepared by mixing 1200 g 8000 MW polyethylene glycol (PEG-8000), 20 g monobasic sodium phosphate (monohydrate) and 71.6 g dibasic phosphate (anhydrous) in approximately 4000 mL water. The pH was then adjusted to about 7.6–7.8 with 1N NaOH and water added to a final volume of 6000 mL.

7. A 6 foot long PVC rinsing trough 2 inches in diameter.

8. Rinse agent: purified water.

9. Drying cabinet with pulleys and heated air blowers.

10. Level wind uptake spool and driver.

B. Extrusion

To a dehydrating trough, approximately 5000 mL of dehydrating agent was poured and the recirculating pump was started. The dehydration agent velocity was maintained about 5 cm/sec to produce a laminar flow of agent along the length of the dehydration trough.

Approximately 400 mL of the rinse agent was added to the rinsing trough.

A needle was placed into the dehydrating agent approximately 12 inches from the upstream end. The collagen syringe barrel was attached to the syringe pump, the pump set at an infusion rate of about 2.5 mL/min, and the infusion pump started.

When enough slack was generated in the dehydration trough, the thread was manually transferred through the rinsing trough and disposed over the first pulley in the drying cabinet. The thread typically sat for about three minutes in the rinsing trough. The heated blower was then turned on to about 35°–40° C. Gradually, as the thread dried, the collagen thread was then carefully disposed over the pulleys in a zigzag fashion. The free end of the formed thread was wound on the uptake spool. The speed of the uptake spool was set so that the thread emerged dry to the touch from the cabinet.

Continuous thread of up to several hundred meters has been produced.

Example 2

Comparison of Stress Relaxation Conditioned Bundles to Non-Stress Relaxation Conditioned Bundles of Varying Ply Reconstituted collagen threads were produced as described in Example 1. Thread bundles of 10, 50 and 200 ply were made by winding collagen thread around two pegs firmly mounted to a frame. At the points where the thread wrapped around the pegs, threads were secured with tape to form a loop. At the tape, the loop ends were cut to form a bundle of threads where each thread was about the same length as the others. The tensions of individual threads, when compared across the bundle, varied.

A Mini-Bionix 858 mechanical testing system (MTS Systems Corp., Eden Prairie, Minn.) was used to test collagen thread bundles. Bundles were fixably fastened in vertically opposing jawgrips where the upper jawgrip pull upward and away from lower positionally fixed jawgrip. Baseline values of tensile strength for dry, non-crosslinked bundles were obtained by pulling the bundles past the breaking point. Bundles broke gradually, one thread at a time, at many places along the gauge length.

To generate a load-elongation curve, bundles were mounted in the grips of the mechanical testing system and saturated with phosphate buffered saline (PBS). The bundles were elongated stepwise to a total strain of about 50% of baseline and allowed to relax to zero load. The bundles were then rinsed in purified water and allowed to dry. All bundles were crosslinked with 2.5% glutaraldehyde. Water rinsed and air dried. Mechanical testing was performed on PBS plasticized bundles at a strain rate of about 50%/minute; peak load was noted.

Denier matched control constructs were fabricated as described above so as to compare constructs of the same denier to the resultant strain conditioned constructs. Strain conditioned (SC) samples were compared both to non strain conditioned samples (NSC) and denier matched controls (DMC) of post-conditioning size. Data were analyzed using Student's t-test, with significance levels of $p>0.05$ (not significant designated "ns"), $p<0.05$, $p<0.01$, and $p<0.001$. The results are shown in Table 1.

TABLE 1

|  | NSC | SC | DMC |
|---|---|---|---|
| 10 PLY | | | |
| Total Size (denier) | 600 | 400 | 400 |
| Mean Peak Load (g) | 642 | 619 | 570 |
| UTS (g/denier) | 1.069 | 1.548 | 1.426 |
| SC % Increase | +45% | | +9% |
| Significance | p < 0.001 | | not significant |
| 50 PLY | | | |
| Total Size (denier) | 3000 | 2000 | 2000 |
| Mean Peak Load (g) | 1633 | 2405 | 1767 |
| UTS (g/denier) | 0.544 | 1.202 | 0.884 |
| SC % Increase | +121% | | +36% |
| Significance | p < 0.001 | | p < 0.001 |
| 200 PLY | | | |
| Total Size (denier) | 12000 | 8000 | 8000 |
| Peak Load (g) | 5294 | 6211 | 4537 |
| UTS (g/denier) | 0.441 | 0.776 | 0.567 |
| SC % Increase | +76% | | +37% |
| Significance | p < 0.001 | | p < 0.05 |

The UTS increase of SC over NSC bundles appears to be due to the improved alignment and the reduction in total cross sectional area (i.e., fiber thinning) caused by the elongation treatment. The UTS increase of SC over DMC appears to be due to improved load sharing, as length, tension, and orientation become more uniform within the bundle. Application of these findings may improve the mechanical properties of a collagenous ACL replacement, and may provide a basis for the development of other types of implants with enhanced mechanical properties.

Example 3

Comparison of Conditioned and Non-Conditioned Collagen Thread Bundles

Reconstituted collagen threads were produced as described in Example 1. Bundles were made by winding 20 plies (20 threads) of 50-denier collagen thread around a frame, securing the ends with tape, and cutting the tape. First, dry samples were tested to get a baseline value of tensile strength of the construct without preconditioning, which is actually the dry strength of the sample. The bundles broke gradually, one thread at a time, in many places within the gauge length, this served as the value for ultimate load (maximum load before breaking).

The bundle was then secured within the pneumatic jaw-grips of a Mini-Bionix 858 mechanical testing system (MTS Systems Corp., Eden Prairie, Minn.) testing machine, and the specimen (approximately 50 mm gauge length) was sprayed with PBS.

The bundle was then rinsed by saturated with purified water, and allowed to dry at room temperature. The bundle was crosslinked by saturating the construct with 2.5% glutaraldehyde in PBS, rinsed with purified water and allowed to dry. Tape was applied to the mid-substance of the test sample, and it was remounted in the MTS, again at approximately 50 mm gauge length. The sample was plasticized with PBS, then tested to failure using a strain rate of about 50%/minute.

Non-conditioned control samples were treated and tested identically, except were not subjected to conditioning.

Mechanical testing results are tabulated as shown in Table 2, comparing non-conditioned controls to conditioned samples. The cross-sectional area of a single non-conditioned wet crosslinked thread was taken to be approximately 0.006 mm$^2$.

TABLE 2

|  | Non-Conditioned Controls | Conditioned Samples |
|---|---|---|
| Max Load | 433 g ± 42 | 423 g ± 90 |
| Total Area | (20)(.006) = 0.120 mm$^2$ | (0.12)/(1.85) = 0.065 mm$^2$ |
| UTS | (0.433)(9.81)/0.12 = 35.4 MPa | (0.423)(9.81)/0.06 = 63.8 MPa |
| Grams per end | 433/20 = 21.6 g/end | 423/20 = 21.2 g/end |
| Denier | (20)(50) = 1000 | (20)(50/1.85) = 540 |
| Wet Tenacity | 433/1000 = 0.433 g/den | 423/540 = 0.783 g/den |

Compared to non-conditioned control samples, constructs that were conditioned demonstrated a much higher tenacity, nearly twice as much. Stress relaxed bundles also exhibit a much higher degree of packing as threads are packed more tightly together.

Example 4

Large Bundle Constructs

Collagen thread bundles totaling about 510-plies were conditioned as previously described. Total strain at conditioning averaged about 26.7%, thus reducing the effective denier to an average of about 40.4 per end (20182 total) within the bundle. Controls were tested without strain conditioning, both dry and PBS-wetted. Pull tests were performed on glutaraldehyde crosslinked samples after plasticizing the threads with PBS. The results are shown in Table 3.

Like other tests on similarly sized materials, breaks often occurred at the jaws; therefore, strength results should be regarded as minimum values.

TABLE 3

| Sample Type | Max Load (grams) | Total Denier (denier) | Wet Tenacity (grams/denier) |
|---|---|---|---|
| Control | 6279 g | 26500 den | 0.251 g/den |
| [Non-wetted, non-strained] | 7279 g | 25000 den | 0.291 g/den |
|  | 7296 g | 25000 den | 0.292 g/den |
| Mean ± SD | 6951 g ± 582 |  | 0.278 g/den ± 0.023 |
| Control | N/A | N/A | N/A |
| [PBS-wetted, non-strained] | 7905 g | 25000 den | 0.316 g/den |
|  | 8325 g | 25000 den | 0.333 g/den |
| Mean ± SD | 8116 g ± 298 |  | 0.325 g/den ± |

TABLE 3-continued

| Sample Type | Max Load (grams) | Total Denier (denier) | Wet Tenacity (grams/denier) |
|---|---|---|---|
| Conditioned samples | 10620 g | 22069 den | 0.012 [p < 0.001] 0.481 g/den |
| [PBS-wetted] | 8150 g | 19290 den | 0.422 g/den |
|  | 9030 g | 19186 den | 0.471 g/den |
| Mean ± SD | 9267 g ± 1251 |  | 0.458 g/den ± 0.032 [p < 0.001] |

Wet tenacity values of these large bundles showed about 17.9% increase on average after wetting and drying with ordinary PBS. This increase is probably due to improved cohesion within the bundle after wetting. Compared to wet controls, strain conditioning of the bundle increased the peak load only about 14.2%, but increased with wet tenacity by about 40.9%, a much greater margin; compared to dry controls, the conditioning caused a significant increase in peak load (about 33.3%) and an even larger increase in wet tenacity (about 64.7%). The tenacity increases are due to both the lowering of the total denier after conditioning and the increasing of peak load.

Stress relaxation conditioning has been shown to increase the wet tenacity of collagen thread bundles up to a content of 500 plies. This increase is attributable to two factors: (1) a decrease in the total denier of the construct resulting from the conditioning strain; (2) an increase in peak load.

Although the foregoing invention has been described in some detail by way of illustration and example for purposes of clarity and understanding, it will be obvious to one of skill in the art that certain changes and modifications may be practiced within the scope of the appended claims.

I claim:

1. A method for increasing the strength of at least one collagen thread, comprising:
   (a) plasticizing a collagen thread with a plasticizing agent;
   (b) imparting a tensile load to the collagen thread by elongation of said collagen thread to impart a strain on the thread;
   (c) allowing the load in the thread to decrease substantially by stress-relaxation or by creep; and
   (d) removing the plasticizing agent from the collagen thread.

2. The method of claim 1, further comprising the step:
   (e) crosslinking the thread.

3. The method of claim 1, wherein the plasticizing agent is water or aqueous buffer.

4. The method of claim 1, wherein the tensile load is imparted by elongation of the thread to a strain between about 20 to 200%.

5. The method of claim 1, wherein the tensile load is applied to produce elongation of the thread to a strain between about 50 to 100%.

6. The method of claim 1, wherein the elongation is done in repeated increments.

7. The method of claim 6, wherein each increment produces a strain of about 5 to 10%.

8. The method of claim 1, wherein the load is decreased by stress-relaxation or creep to less than 0.5 grams.

9. The method of claim 2, wherein the crosslinking is accomplished by lyophilization or ultraviolet (UV) irradiation or by a crosslinking agent selected from the group consisting of acyl-azide, hexamethylene diisocyanate, bisimidates, glyoxal, polyglycerol polyglycidyl ether, adipyl chloride, ribose and other sugars, carbodiimides, and aldehydes.

10. The method of claim 9, wherein the crosslinking agent is 1-ethyl-3-(3-dimethylaminopropyl) carbodiimide hydrochloride (EDC).

11. A method for increasing the strength of a multi-ply bundle of collagen threads, comprising:
    (a) plasticizing a multi-ply bundle of collagen threads with water, an aqueous buffered solution, or glycerol;
    (b) imparting a tensile load to said multi-ply bundle by elongating the said bundle to impart a strain on said multi-ply bundle;
    (c) allowing the load in said multi-ply bundle to decrease substantially by stress-relaxation or by creep; and,
    (d) removing the plasticizing agent from said multi-ply bundle.

12. The method of claim 11, wherein the tensile load is applied to produce elongation of the thread to a strain between about 20 to 200%.

13. The method of claim 11, wherein the tensile load is applied to produce elongation of the thread to a strain between about 50 to 100%.

14. The method of claim 11, wherein said elongation is done in repeated increments.

15. The method of claim 14, wherein the each increment produces a strain of about 5% to about 10%.

16. The method of claim 11, further comprising the step of:
    (e) crosslinking said multi-ply bundle.

17. The method of claim 16, further comprising the step of:
    (f) sterilizing said crosslinked multi-ply bundle.

18. The method of claim 17, further comprising the step of:
    (g) coating said multi-ply bundle with pharmaceuticals, growth factors, hormones, extracellular matrix components, or genetic material.

19. The method of claim 16, wherein the crosslinking is accomplished by crosslinking agent 1-ethyl-3-(3-dimethylaminopropyl) carbodiimide hydrochloride (EDC).

20. The method of claim 11, wherein the multi-ply bundle is between 2 and 1000 ply.

21. The method of claim 11, wherein the multi-ply bundle is between 20 and 500 ply.

22. A method for increasing the strength of a multi-ply bundle of collagen threads, comprising:
    (a) plasticizing a multi-ply bundle of collagen threads of between 2 and 1000-ply with a plasticizing agent selected from the group consisting of water, an aqueous buffered solution, or glycerol;
    (b) imparting a tensile load to said multi-ply bundle by elongating the said bundle to impart a strain on said multi-ply bundle of about 5% to about 10%;
    (c) allowing the load in said multi-ply bundle to decrease by stress-relaxation or by creep to less than 0.5 grams;
    (d) repeating said elongation in repeated increments;
    (e) removing the plasticizing agent from said multi-ply bundle;
    (f) crosslinking said multi-ply bundle; and,
    (g) sterilizing said crosslinked bundle.

* * * * *